US009675579B2

(12) United States Patent
Rock et al.

(10) Patent No.: US 9,675,579 B2
(45) Date of Patent: Jun. 13, 2017

(54) TETRAHYDROCANNABIVARIN FOR USE IN THE TREATMENT OF NAUSEA AND VOMITING

(71) Applicant: GW Pharma Limited, Salisbury, Wiltshire (GB)

(72) Inventors: Erin Rock, Guelph (CA); Linda Parker, Guelph (CA); Marnie Duncan, Salisbury (GB); Colin Stott, Salisbury (GB)

(73) Assignee: GW Pharma Limited, Cambridge (GB)

(*) Notice: Subject to any disclaimer, the term of this patent is extended or adjusted under 35 U.S.C. 154(b) by 0 days.

(21) Appl. No.: 14/785,055

(22) PCT Filed: Apr. 14, 2014

(86) PCT No.: PCT/GB2014/051159
§ 371 (c)(1),
(2) Date: Oct. 16, 2015

(87) PCT Pub. No.: WO2014/170649
PCT Pub. Date: Oct. 23, 2014

(65) Prior Publication Data
US 2016/0074357 A1    Mar. 17, 2016

(30) Foreign Application Priority Data
Apr. 18, 2013  (GB) ................................. 1307047.9

(51) Int. Cl.
A61K 31/352   (2006.01)

(52) U.S. Cl.
CPC .................................. A61K 31/352 (2013.01)

(58) Field of Classification Search
CPC ..................................................... A61K 31/352
See application file for complete search history.

(56) References Cited

U.S. PATENT DOCUMENTS

2005/0165088 A1* 7/2005 Whittle .................. A61K 31/05
                                                            514/454
2010/0317729 A1* 12/2010 Guy ....................... A61K 31/05
                                                            514/454

FOREIGN PATENT DOCUMENTS

| GB | 2 384 707 A | 8/2003 | |
| GB | 2 478 595 A | 9/2011 | |
| GB | 2 494 461 A | 3/2013 | |
| WO | WO 2011110866 A1 * | 9/2011 | ............. A61K 31/05 |

OTHER PUBLICATIONS

Beyer et al., Depression-like phenotype following chronic CB1 receptor antagonism. Neurobiol Dis. Aug. 2010;39(2):148-55. doi: 10.1016/j.nbd.2010.03.020. Epub Apr. 8, 2010.
(Continued)

Primary Examiner — Theodore R West
(74) Attorney, Agent, or Firm — Wolf, Greenfield & Sacks, P.C.

(57) ABSTRACT

The present invention relates to the use of tetrahydrocannabivarin (THCV) in the treatment of nausea and vomiting. Preferably the THCV is isolated and/or purified from cannabis plant extracts. Preferably the nausea and/or vomiting is caused by the effects of a medication such as a chemotherapeutic agent.

12 Claims, 2 Drawing Sheets

(56) References Cited

OTHER PUBLICATIONS

Bolognini et al., The plant cannabinoid Delta9-tetrahydrocannabivarin can decrease signs of inflammation and inflammatory pain in mice. Br J Pharmacol. Jun. 2010;160(3):677-87. doi:10.1111/j.1476-5381.2010.00756.x.

De Mattos Viana et al., Melancholic features related to rimonabant. Gen Hosp Psychiatry. Nov.-Dec. 2009;31(6):583-5. doi:10.1016/j.genhosppsych.2008.12.009. Epub Feb. 20, 2009.

Després, Pleiotropic effects of rimonabant: clinical implications. Curr Pharm Des. 2009;15(5):553-70.

García et al., Symptom-relieving and neuroprotective effects of the phytocannabinoid $\Delta^9$-THCV in animal models of Parkinson's disease. Br J Pharmacol. Aug. 2011;163(7):1495-506. doi:10.1111/j.1476-5381.2011.01278.x.

Hill et al., $\Delta^9$-Tetrahydrocannabivarin suppresses in vitro epileptiform and in vivo seizure activity in adult rats. Epilepsia. Aug. 2010;51(8):1522-32. doi: 10.1111/j.1528-1167.2010.02523.x. Epub Feb. 26, 2010.

Limebeer et al., Delta-9-tetrahydrocannabinol interferes with the establishment and the expression of conditioned rejection reactions produced by cyclophosphamide: a rat model of nausea. Neuroreport. Dec. 16, 1999;10(18):3769-72.

Limebeer et al., Effect of 5-HT3 antagonists and a 5-HT(1A) agonist on fluoxetine-induced conditioned gaping reactions in rats. Psychopharmacology (Berl). May 2009;203(4):763-70. doi:10.1007/s00213-008-1421-3. Epub Dec. 10, 2008.

Limebeer et al., Inverse agonism of cannabinoid CB1 receptors potentiates LiCl-induced nausea in the conditioned gaping model in rats. Br J Pharmacol. Sep. 2010;161(2):336-49. doi:10.1111/j.1476-5381.2010.00885.x.

Mclaughlin et al., The cannabinoid CB1 antagonist AM 251 produces food avoidance and behaviors associated with nausea but does not impair feeding efficiency in rats. Psychopharmacology (Berl). Jul. 2005;180(2):286-93. Epub Mar. 15, 2005.

Parker et al., Cannabidiol, a non-psychoactive component of cannabis and its synthetic dimethylheptyl homolog suppress nausea in an experimental model with rats. Neuroreport. Apr. 16, 2002;13(5):567-70.

Parker et al., Cannabinoid agonists and antagonists modulate lithium-induced conditioned gaping in rats. Integr Physiol Behav Sci. Apr.-Jun. 2003;38(2):133-45.

Parker et al., Conditioned nausea in rats: assessment by conditioned disgust reactions, rather than conditioned taste avoidance. Can J Exp Psychol. Sep. 2008;62(3):198-209. doi: 10.1037/a0012531.

Parker et al., Effects of cannabinoids on lithium-induced conditioned rejection reactions in a rat model of nausea. Psychopharmacology (Berl). Mar. 2003;166(2):156-62. Epub Jan. 15, 2003.

Pertwee et al., The psychoactive plant cannabinoid, Delta9-tetrahydrocannabinol, is antagonized by Delta8- and Delta9-tetrahydrocannabivarin in mice in vivo. Br J Pharmacol. Mar. 2007;150(5):586-94. Epub Jan. 22, 2007.

Pertwee, The diverse CB1 and CB2 receptor pharmacology of three plant cannabinoids: delta9-tetrahydrocannabinol, cannabidiol and delta9-tetrahydrocannabivarin. Br J Pharmacol. Jan. 2008;153(2):199-215.

Riedel et al., Synthetic and plant-derived cannabinoid receptor antagonists show hypophagic properties in fasted and non-fasted mice. Br J Pharmacol. Apr. 2009;156(7):1154-66.

Rock et al., Evaluation of the potential of the phytocannabinoids, cannabidivarin (CBDV) and $\Delta(9)$-tetrahydrocannabivarin (THCV), to produce CB1 receptor inverse agonism symptoms of nausea in rats. Br J Pharmacol. Oct. 2013;170(3):671-8. doi: 10.1111/bph.12322.

Sink et al., Potential anxiogenic effects of cannabinoid CB1 receptor antagonists/inverse agonists in rats: comparisons between AM4113, AM251, and the benzodiazepine inverse agonist FG-7142. Eur Neuropsychopharmacol. Feb. 2010;20(2):112-22. doi:10.1016/j.euroneuro.2009.11.002. Epub Dec. 16, 2009.

Sink et al., The novel cannabinoid CB1 receptor neutral antagonist AM4113 suppresses food intake and food-reinforced behavior but does not induce signs of nausea in rats. Neuropsychopharmacology. Mar. 2008;33(4):946-55. Epub Jun. 20, 2007. Erratum in: Neuropsychopharmacology. Jun. 2008;33(7):1776. Pang, Yan [corrected to Peng, Yan]; Olzewska, Teresa [corrected to Olszewska, Teresa].

Thomas et al., Cannabidiol displays unexpectedly high potency as an antagonist of CB1 and CB2 receptor agonists in vitro. Br J Pharmacol. Mar. 2007;150(5):613-23. Epub Jan. 22, 2007.

Thomas et al., Evidence that the plant cannabinoid Delta9-tetrahydrocannabivarin is a cannabinoid CB1 and CB2 receptor antagonist. Br J Pharmacol. Dec. 2005;146(7):917-26.

Westfall, Use of anti-emetic herbs in pregnancy: women's choices, and the question of safety and efficacy. Complement Ther Nurs Midwifery. Feb. 2004;10(1):30-6.

\* cited by examiner

TETRAHYDROCANNABIVARIN FOR USE IN THE TREATMENT OF NAUSEA AND VOMITING

RELATED APPLICATION

This application is a national stage filing under 35 U.S.C. §371 of international application PCT/GB2014/051159, filed Apr. 14, 2014, which was published under PCT Article 21 (2) in English The present invention relates to the use of tetrahydrocannabivarin (THCV) in the treatment of nausea and vomiting. Preferably the THCV is isolated and/or purified from cannabis plant extracts.

BACKGROUND TO THE INVENTION

Side effects of the $CB_1$ receptor inverse agonist/antagonist, rimonabant (SR141716; SR), in humans include nausea and depression (de Mattos Viana et al., 2009; Despres, 2009). The nausea produced by SR and another compound AM251 (McLaughlin et al., 2005) is the result of the inverse agonism at the $CB_1$ receptor (Sink et al., 2008). Equivalent doses of AM251 produced conditioned gaping in rats.

The conditioned gaping model (see Parker et al., 2008 for review) has been shown to detect the nauseating side effect of several compounds, including selective serotonin reuptake inhibitors (SSRIs), phosphodiesterase-4 inhibitors and $CB_1$ receptor inverse agonists (McLaughlin et al., 2005; Sink et al., 2008).

As well as producing nausea on their own, the $CB_1$ receptor inverse agonists (at sub-threshold doses that do not produce nausea on their own), SR (Parker et al., 2003) and AM251 (Limebeer et al., 2010), potentiate the nausea produced by the toxin lithium chloride (LiCl).

Phytocannabinoids have recently become candidates for therapeutic applications, however their usefulness may be limited if they exhibit nausea producing effects. Much of the research on phytocannabinoids has concentrated on the psychoactive compound, THC and, the primary non-psychoactive cannabinoid, cannabidiol (CBD), found in marijuana. Low doses (0.5 mg/kg THC and 5 mg/kg CBD) of both of these compounds have been shown to suppress toxin-induced conditioned gaping in the rodent model of conditioned nausea (Limebeer & Parker 1999; Parker et al., 2002; Parker et al., 2003).

The effects of phytocannabinoid tetrahydrocannabivarin (THCV) in the rodent model of conditioned nausea were unknown.

Recent work with both plant-derived THCV and synthetic THCV (0-4394) has elucidated its behavioural effects and mechanism of action. In vitro, THCV acts as a $CB_1$ and $CB_2$ receptor antagonist (Thomas et al., 2005).

In vivo, THCV has also been shown to act as a $CB_1$ receptor antagonist at low doses (<3 mg/kg) (Pertwee et al., 2007). THCV shares the ability of AM251 to reduce the food intake and body weight of non-fasted and fasted mice (Robinson et al., 2007).

THCV has been shown to suppress seizure activity (Hill et al., 2010), reduce inflammation and inflammatory pain (Bolognini et al., 2010), reduce weight due to hypophagia (Riedel et al., 2009), it is also able to reduce Parkinson's disease symptoms, as well as disease progression (Garcia et al., 2011). Therefore, further examination of potential nauseating side effects of THCV is important.

The patent GB2384707B describes the anti-emetic effect of CBD and CBDA using the suncus murinus model of nausea.

The applicants have evaluated whether the phytocannabinoid produced nausea and potentiate toxin-induced nausea. Because it is known that THCV can behave as a CB1 antagonist and shares the ability of SR and AM251 to reduce food intake in vivo it was likely that this phytocannabinoid would produce nausea and potentiate toxin-induced nausea.

Surprisingly the applicants have discovered that THCV neither produced nausea nor potentiated toxin-induced nausea and more significantly at high doses actually acted as an anti-emetic. As such THCV is a potential candidate for use in the treatment of nausea and vomiting.

BRIEF SUMMARY OF THE DISCLOSURE

In accordance with a first aspect of the present invention there is provided the phytocannabinoid tetrahydrocannabivarin (THCV) for use in the treatment of nausea and/or vomiting.

Preferably the nausea and/or vomiting are caused by the effects of a medication.

More preferably the medication is a chemotherapeutic medicine.

Preferably the THCV is present in an effective human daily dose to reduce or relieve nausea and/or vomiting.

The human dose equivalent (HED) can be estimated using the following formula:

$$HED = \text{Animal dose (mg/kg) multiplied by} \frac{\text{Animal } K_m}{\text{Human } K_m}$$

The $K_m$ for a rat is 6 and the $K_m$ for a human is 37.

More preferably the effective human daily dose of THCV is between 1 mg and 2000 mg. More preferably still the effective human daily dose of THCV is between 10 mg and 1000 mg. Most preferably greater than or equal to 50 mg, through 75 mg, through 100 mg, to 150 mg of THCV.

Preferably the THCV is packaged for use for an extended treatment period.

More preferably the extended treatment period is at least 7 days.

The THCV may be provided in combination with one or more other medicinal substances.

The THCV may be in an isolated or substantially pure form. Alternatively the THCV may be in the form of a botanical drug substance (BDS).

When the THCV is in the form of a BDS, preferably all or a substantial proportion of tetrahydrocannabinol (THC) has been removed.

In accordance with a second aspect of the present invention there is provided the phytocannabinoid tetrahydrocannabivarin (THCV) in combination with a chemotherapeutic agent.

Preferably the chemotherapeutic agent is a cannabinoid chemotherapeutic agent, alternatively the chemotherapeutic agent is a non-cannabinoid chemotherapeutic agent.

In accordance with a third aspect of the present invention there is provided the phytocannabinoid tetrahydrocannabivarin (THCV) in an amount between 1 and 2000 mg in combination with a chemotherapeutic agent.

In this specification the following terms are used and are intended to have the following meanings/definitions:

"Cannabinoids" are a group of compounds including the endocannabinoids, the phytocannabinoids and those which are neither endocannabinoids nor phytocannabinoids, hereafter "syntho-cannabinoids".

"Endocannabinoids" are endogenous cannabinoids, which are high affinity ligands of CB1 and CB2 receptors.

"Phytocannabinoids" are cannabinoids that originate in nature and can be found in the cannabis plant. The phytocannabinoids can be present in an extract including a botanical drug substance, isolated, or reproduced synthetically.

"Syntho-cannabinoids" are those compounds capable of interacting with the cannabinoid receptors (CB1 and/or CB2) but are not found endogenously or in the cannabis plant. Examples include WIN 55212 and SR141716 (rimonabant).

An "isolated phytocannabinoid" is one which has been extracted from the cannabis plant and purified to such an extent that all the additional components such as secondary and minor cannabinoids and the non-cannabinoid fraction have been removed.

A "synthetic cannabinoid" is one which has been produced by chemical synthesis this term includes modifying an isolated phytocannabinoid, by for example forming a pharmaceutically acceptable salt thereof.

A "botanical drug substance" or "BDS" is defined in the Guidance for Industry Botanical Drug Products Guidance, June 2004, US Department of Health and Human Services, Food and Drug Administration Centre for Drug Evaluation and Research as: "A drug derived from one or more plants, algae, or microscopic fungi. It is prepared from botanical raw materials by one or more of the following processes: pulverisation, decoction, expression, aqueous extraction, ethanolic extraction or other similar processes." A botanical drug substance does not include a highly purified or chemically modified substance derived from natural sources. Thus, in the case of cannabis, BDS derived from cannabis plants do not include highly purified Pharmacopoeial grade cannabinoids The structure of the phytocannabinoid THCV is as shown below:

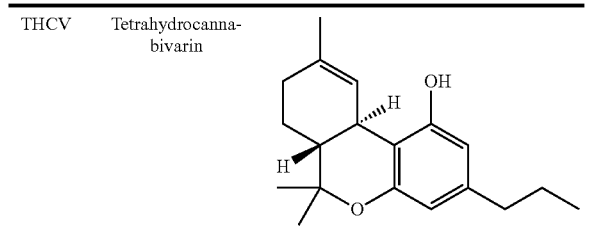

THCV   Tetrahydrocannabivarin

For the purpose of this invention the term 'treatment' is intended to encompass reducing vomiting and nausea. Such agents are often known as "antiemetics". Antiemetics are typically used to treat or reduce vomiting and/or nausea caused by illnesses such as gastroparesis, migraine, rotavirus, vertigo, viral gastroenteritis and other illnesses that cause nausea and/or vomiting, motion sickness, or the side effects of medications such as opioid analgesics, general anesthetics and chemotherapy. A therapeutically effective amount is an amount of phytocannabinoid that achieves this aim.

BRIEF DESCRIPTION OF THE DRAWINGS

Embodiments of the invention are further described hereinafter with reference to the accompanying drawings, in which.

DETAILED DESCRIPTION

Figure 1:
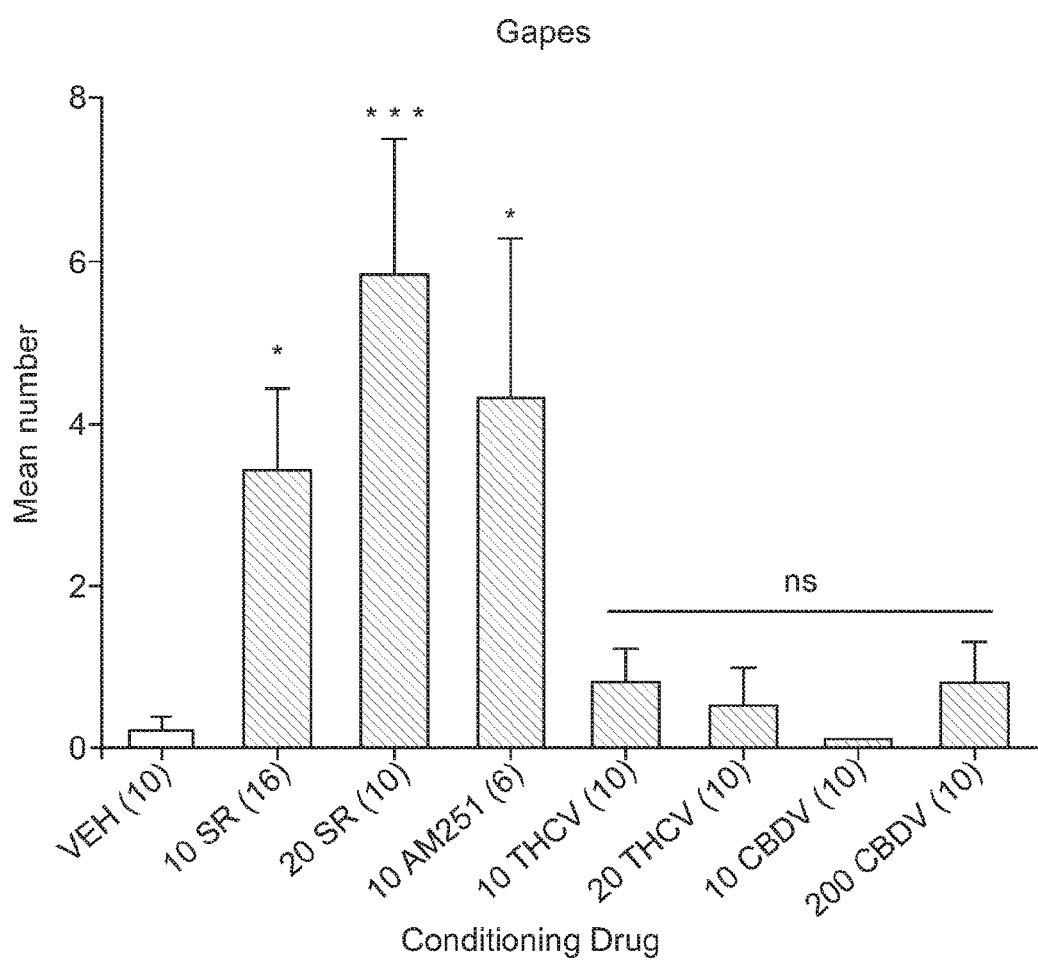
FIG. 1 shows the mean number (±sem) of gapes at test elicited by 0.1% saccharin solution previously paired with each compound during the drug-free test trial.

The compounds SR141716 (SR) and AM251 produce nausea and potentiate toxin-induced nausea. Here, the phytocannabinoid, tetrahydrocannabivarin (THCV) was evaluated to determine whether it also produced nausea and potentiated toxin-induced nausea.

The Examples below demonstrate the effectiveness of the phytocannabinoid in the rodent model of conditioned nausea.

If a compound produces nausea it is expected to: 1) produce conditioned gaping reactions to a novel flavour with which it is paired (Example 1), and 2) enhance the nauseating effects of another toxin, i.e., producing potentiation of LiCl-induced conditioned gaping (Example 2).

If THCV does not produce gaping and does not enhance LiCl-induced gaping, it is likely that this compound will be useful in the treatment of nausea and vomiting.

EXAMPLE 1

THE Potential of THCV to Produce Conditioned Gaping

Materials and Methods

Animals: Procedures were according to the Canadian Council on Animal Care (CCAC). The protocol was approved by the Institutional Animal Care Committee, which is accredited by the CCAC.

Naïve male Sprague-Dawley rats, obtained from Charles River Laboratories (St Constant, Quebec) were single-housed in shoebox cages in the colony room at an ambient temperature of 21° C. with a 12/12 light/dark schedule (lights off at 8 AM) and maintained on ad-libitum food and water.

Drugs and Materials: All cannabinoid compounds were prepared in a vehicle (VEH) of ethanol/Cremophor (Sigma)/saline (SAL; 1:1:18) and administered intraperitonally (i.p.). LiCl (Sigma) was prepared in a 0.15 M solution with sterile water and administered i.p. at a volume of 20 ml/kg (127.2 mg/kg) in Example 2.

SR was prepared at 2.5, 10 and 20 mg/kg and administered at a volume of 2 ml/kg. CBDV was prepared at 2.5 and 10 mg/kg and administered at a volume of 2 ml/kg. A high dose of CBDV was prepared at 200 mg/kg and administered at a volume 10 ml/kg. THCV was prepared at 2.5, 10 and 20 mg/kg and administered at a volume of 2 ml/kg. AM251 was prepared at 10 mg/kg and administered at a volume of 2 ml/kg. THC was prepared at 2.5 and 10 mg/kg and administered at a volume of 2 ml/kg.

Procedures: Rats were implanted with intraoral cannulae under isofluorane anesthesia. Following recovery from surgery (at least 3 days), the rats received an adaptation trial in which they were placed in the taste reactivity (TR) chamber with their cannula attached to an infusion pump for fluid delivery. Water was infused into their intraoral cannula for 2 min at the rate of 1 ml/min.

The TR chambers were made of clear Plexiglas (22.5× 26×20 cm) that sat on a table with a clear glass top. A mirror beneath the chamber on a 45° angle facilitated viewing of the ventral surface of the rat to observe orofacial responses.

On the day following the adaptation trial, the rats received a conditioning trial during which they were intraorally infused with 0.1% saccharin solution for 2 min at the rate of 1 ml/min. Immediately after the saccharin infusion, they (n=10/group, except AM251 with n=6) were injected with either: VEH (1/1/18: alcohol/cremaphor/saline), 10 mg/kg SR, 20 mg/kg SR, 10 mg/kg AM251, 10 mg/kg THCV, 20 mg/kg THCV, 10 mg/kg CBDV or 200 mg/kg CBDV.

Seventy two hours after the conditioning trial, the rats were returned to the TR chamber and intraorally infused with 0.1% saccharin solution and their orofacial reactions were video recorded with the feed from the video camera fire-wired into a computer. The video tapes are later scored (at ½speed) by a trained observer blind to the experimental conditions for the behaviour of gaping (large openings of the mouth and jaw, with lower incisors exposed). The videotapes were scored by 2 trained raters, resulting in an extremely high inter-rater reliability score (r=0.97).

Results

The $CB_1$ inverse agonists/antagonists, SR and AM251, produced more conditioned gaping reactions (nausea-like reactions) than any other group and none of the other drugs tested produced gaping that differed from VEH controls.

FIG. 1 presents the mean (±sem) number of gapes displayed by the various groups in Example 1. The one-way analysis of variance (ANOVA) revealed a main effect of group, $F(7, 74)=4.9$; $p<0.001$.

By LSD comparison tests, all doses of the $CB_1$ inverse agonists/antagonists (SR and AM251) produced significantly more conditioned gaping when paired with saccharin solution than any of the other compounds ($p$'s$<0.05$).

As well, none of the other compounds (at any dose tested) significantly differed from VEH controls. SR produced marginally more gaping at 20 mg/kg than at 10 mg/kg ($p=0.057$).

At all doses tested, THCV did not produce apparent inverse agonist properties when compared with VEH, but SR and AM251 both produced the inverse agonist effect of nausea that is not produced by receptor neutral $CB_1$ antagonists.

Conclusion

The results of Example 1 revealed that when explicitly paired with a novel saccharin solution, neither CBDV (10 or 200 mg/kg) nor THCV (10 or 20 mg/kg) produced the nausea-like profile of conditioned gaping produced by the $CB_1$ receptor inverse agonists, SR and AM251.

Since conditioned gaping in rats is produced only by compounds that produce nausea and emesis in other species (see Parker and Limebeer, 2008), these results suggest that THCV should not cause nausea, an effect that appears to be caused by the $CB_1$ inverse agonist effects of SR and AM251.

EXAMPLE 2

The Potential of THCV to Potentiate Conditioned Gaping Caused By LiCl

Materials and Methods

Animals and Drugs and Materials were as described in Example 1 above.

Following recovery from intraoral cannulation surgery, the rats received the adaptation trial to the TR test as described in Example 1 above. On the day of conditioning (saccharin palatability test), the rats were injected with VEH (n=10), 2.5 mg/kg SR (n=10), 2.5 mg/kg THC (n=6), 10 mg/kg THC (n=7), 2.5 mg/kg THCV (n=10) or 10 mg/kg THCV (n=6), 2.5 mg/kg CBDV (n=10) or 200 mg/kg CBDV (n=13). Thirty min later, each rat was intraorally infused with 0.1% saccharin solution while their orofacial responses were video recorded from the mirror beneath the chamber. Immediately following the 2 min intraoral infusion of saccharin, the rats were injected with 20 ml/kg or 0.15 M LiCl.

Seventy-two hours later, the rats received a drug-free test trial, during which they received a 2 min intraoral infusion of 0.1% saccharin solution and the frequency of gaping was measured. The videotapes were later scored (at ½speed) by an observer blind to the experimental conditions for the hedonic reaction of tongue protrusions (at conditioning and testing). As well, to determine other non-specific effects of the drug during conditioning, the conditioning tapes were scored for bouts of active locomotion (forward movement of paws on the floor of the cage).

Results

Figure 2:
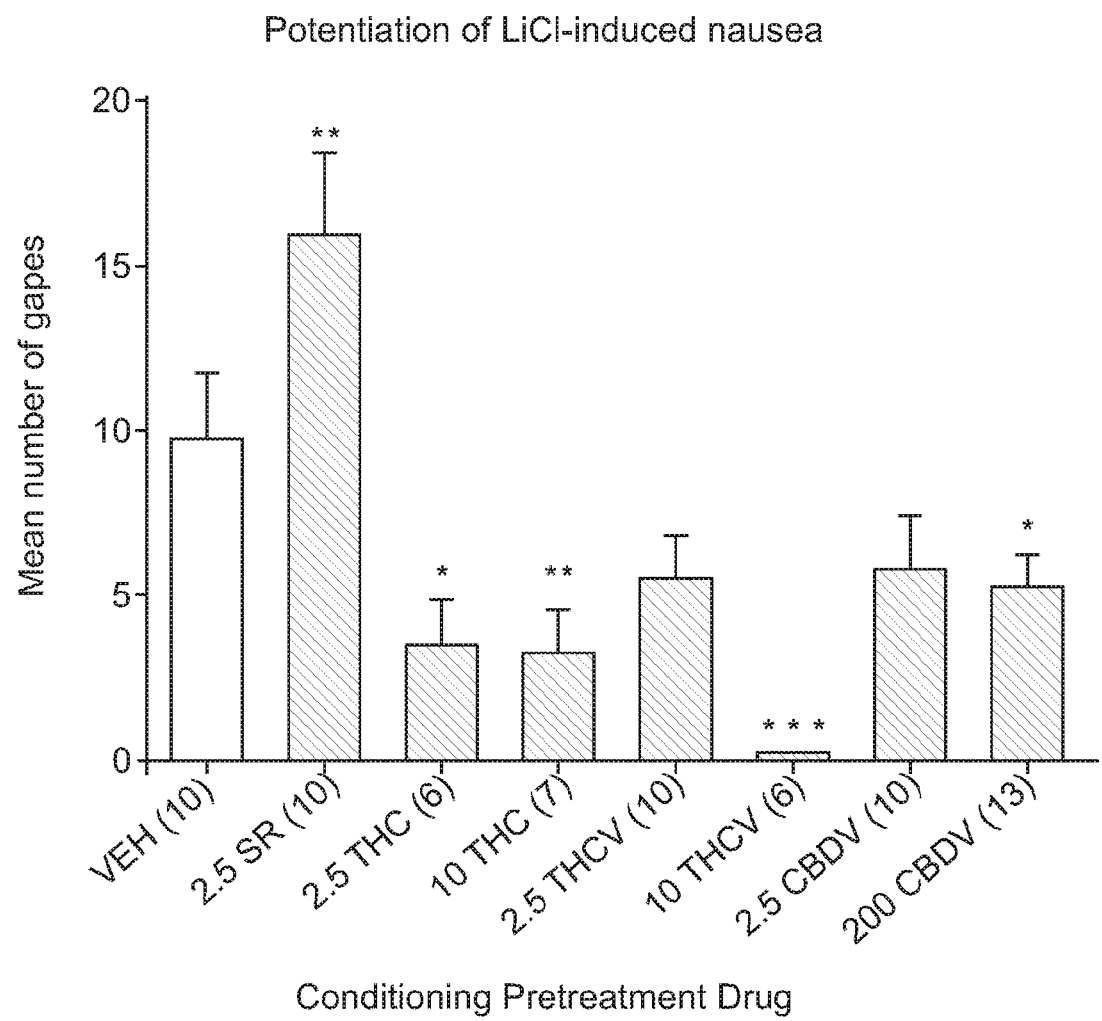
FIG. 2 shows the mean number (±sem) of gapes elicited by 0.1% saccharin solution previously paired with LiCl during the drug-free TR test trial.

FIG. 2 presents the mean (±sem) number of conditioned gaping reactions during the drug-free test, 72 hr following the conditioning trial. The one-way ANOVA revealed a significant group effect, $F(7, 62)=8.0$; $p<0.001$.

Subsequent LSD tests revealed that only Group 2.5 SR displayed potentiated LiCl-induced gaping reactions relative to group VEH ($p<0.025$).

Significantly the group that received 10 mg/kg THCV displayed no gaping reactions ($p<0.001$).

The groups that received 2.5 mg CBDV ($p=0.08$) or 2.5 mg THCV ($p=0.07$) showed marginally attenuated LiCl-induced gaping reactions relative to group VEH.

The groups that received 200 mg CBDV ($p<0.05$), 2.5 mg THC ($p<0.02$) or 10 mg THC ($p<0.01$) significantly attenuated the LiCl-induced gaping reactions.

2.5 mg THCV ($p=0.07$) showed marginally attenuated LiCl-induced gaping reactions relative to group VEH.

This pattern of results suggests that the only compound that enhanced LiCl-induced nausea was 2.5 mg/kg of SR141716.

At a dose of 10 mg/kg, THCV actually eliminated LiCl-induced nausea, to a much greater degree than an equivalent dose of THC, with the added benefit that THCV is not psychoactive like THC. A dose of 200 mg/kg CBDV produced a statistically significant anti-nausea effect, but this effect was less than that produced by the high dose of THCV.

Conclusion

This Example evaluated the potential of THCV to potentiate nausea produced by LiCl. At doses sub-threshold for producing nausea on their own (2.5 mg/kg), both SR (Parker and Mechoulam, 2003) and AM251 (Limebeer et al., 2010) pre-treatments prior to a saccharin-LiCl pairing potentiated the nausea produced by LiCl, as shown by potentiated gaping displayed in the subsequent drug-free test trial 72 hours after conditioning.

The group that was pre-treated with 2.5 mg/kg SR showed potentiated gaping relative to all other groups The THCV, CBDV or THC pre-treated groups displayed attenuated LiCl-induced gaping reactions relative to VEH.

Interestingly, the group that received 10 mg/kg THCV showed no gaping reactions during intraoral infusion of saccharin that had been previously paired with LiCl, suggesting that it completely blocked LiCl-induced nausea, an effect evident with drugs that are anti-nausea agents such as ondansetron.

At a low dose (2.5 mg/kg) THCV acts as a $CB_1$ receptor antagonist (Thomas et al, 2005) and does not enhance LiCl-induced nausea evidenced as potentiation of gaping (like AM4113), suggesting that it is a neutral antagonist.

On the other hand, at a higher doses of THCV (e.g. 10 mg/kg), LiCl-induced gaping was suppressed.

Overall Conclusion

In conclusion, at all doses tested, unlike SR and AM251, THCV neither: 1) produced conditioned gaping on its own when explicitly paired with saccharin solution, nor 2) potentiated LiCl-induced conditioned gaping.

THCV produced an anti-nausea-like effect in Example 2; that is THCV blocked LiCl-induced nausea at a dose greater than 2.5 mg/kg (in rats). This would equate to a human equivalent dose of greater than 0.4 mg/kg.

Taken together, these results suggest that that THCV may be a promising therapeutic, devoid of symptoms associated with $CB_1$ receptor inverse agonism and without the psychotropic effect associated with $CB_1$ agonism.

THCV is as such a potential candidate for use in the treatment of nausea.

REFERENCES

Beyer C E, Dwyer J M, Piesla M J, Platt B J, Shen R, Rahman Z, et al. (2010). Depression-like phenotype following chronic CB1 receptor antagonism. Neurobiol Dis 39: 148-155.

Bolognini D, Costa B, Maione S, Comelli F, Marini P, Di Marzo V, et al. (2010). The plant cannabinoid Delta9-tetrahydrocannabivarin can decrease signs of inflammation and inflammatory pain in mice. Br J Pharmacol 160: 677-687.

de Mattos Viana B, Prais H A & Daker M V (2009). Melancholic features related to rimonabant. Gen Hosp Psychiatry 31: 583-585.

Despres J P (2009). Pleiotropic effects of rimonabant: clinical implications. Curr Pharm Des 15: 553-570.

Garcia C, Palomo-Garo C, Garcia-Arencibia M, Ramos J, Pertwee R & Fernandez-Ruiz J (2011). Symptom-relieving and neuroprotective effects of the phytocannabinoid Delta-THCV in animal models of Parkinson's disease. Br J Pharmacol 163: 1495-1506.

Hill A J, Weston S E, Jones N A, Smith I, Bevan S A, Williamson E M, et al. (2010). Delta-Tetrahydrocannabivarin suppresses in vitro epileptiform and in vivo seizure activity in adult rats. Epilepsia 51: 1522-1532.

Limebeer C L, Litt D E & Parker L A (2009). Effect of 5-HT3 antagonists and a 5-HT(1A) agonist on fluoxetine-induced conditioned gaping reactions in rats. Psychopharmacology (Berl) 203: 763-770.

Limebeer C L, Parker L A (1999). Delta-9-tetrahydrocannabinol interferes with the establishment and the expression of conditioned rejection reactions produced by cyclophosphamide: a rat model of nausea. Neuroreport 10: 3769-3772.

Limebeer C L, Vemuri V K, Bedard H, Lang S T, Ossenkopp K P, Makriyannis A, et al. (2010). Inverse agonism of cannabinoid CB1 receptors potentiates LiCl-induced nausea in the conditioned gaping model in rats. Br J Pharmacol 161: 336-349.

McLaughlin P J, Winston K M, Limebeer C L, Parker L A, Makriyannis A & Salamone J D (2005). The cannabinoid CB1 antagonist AM 251 produces food avoidance and behaviors associated with nausea but does not impair feeding efficiency in rats. Psychopharmacology (Berl) 180: 286-293.

Parker L A, Limebeer C L (2008). Cannabinoids in the management of nausea and vomiting In: Kofalvi A (ed). Cannabinoids and the Brain. Springer: NY, pp 259-273.

Parker L A, Mechoulam R (2003). Cannabinoid agonists and antagonists modulate lithium-induced conditioned gaping in rats. Integr Physiol Behav Sci 38: 133-145.

Parker L A, Mechoulam R & Schlievert C (2002). Cannabidiol, a non-psychoactive component of cannabis and its synthetic dimethylheptyl homolog suppress nausea in an experimental model with rats. Neuroreport 13: 567-570.

Parker L A, Mechoulam R, Schlievert C, Abbott L, Fudge M L & Burton P (2003). Effects of cannabinoids on lithium-induced conditioned rejection reactions in a rat model of nausea. Psychopharmacology (Berl) 166: 156-162.

Parker L A, Rana S A & Limebeer C L (2008). Conditioned nausea in rats: assessment by conditioned disgust reactions, rather than conditioned taste avoidance. Can J Exp Psychol 62: 198-209.

Pertwee R G, Thomas A, Stevenson L A, Ross R A, Varvel S A, Lichtman A H, Martin B R, Razdan R K (2007) The psychoactive plant cannabinoid, $\Delta^9$-tetrahydrocannabinol, is antagonized by $\Delta^8$- and $\Delta^9$-tetrahydrocannabivarin in mice in vivo. Br J Pharmcol, 150: 586-594.

Riedel G, Fadda P, McKillop-Smith S, Pertwee R G, Platt B & Robinson L (2009). Synthetic and plant-derived cannabinoid receptor antagonists show hypophagic properties in fasted and non-fasted mice. Br J Pharmacol 156: 1154-1166.

Sink K S, McLaughlin P J, Wood J A, Brown C, Fan P, Vemuri V K, et al. (2008). The novel cannabinoid CB1 receptor neutral antagonist AM4113 suppresses food intake and food-reinforced behavior but does not induce signs of nausea in rats. Neuropsychopharmacology 33: 946-955.

Sink K S, Segovia K N, Sink J, Randall P A, Collins L E, Correa M, et al. (2010). Potential anxiogenic effects of cannabinoid CB1 receptor antagonists/inverse agonists in rats: comparisons between AM4113, AM251, and the benzodiazepine inverse agonist FG-7142. Eur Neuropsychopharmacol 20: 112-122.

Thomas A, Stevenson L A, Wease K N, Price M R, Baillie G, Ross R A, et al. (2005). Evidence that the plant cannabinoid Delta9-tetrahydrocannabivarin is a cannabinoid CB1 and CB2 receptor antagonist. Br J Pharmacol 146: 917-926.

Thomas A., Baillie G L, Phillips A M, Razdan R K, Ross R A, Pertwee R G (2007). Cannabidiol displays unexpectedly high potency as an antagonist of CB1 and CB2 receptor agonists. Br J Pharmacol 150: 613-623.

The invention claimed is:

1. A method for treating nausea and/or vomiting comprising administering to a subject in need thereof a therapeutically effective amount of a phytocannabinoid tetrahydrocannabivarin (THCV), wherein cannabidiol (CBD) and cannabidivarin (CBDV) are not administered to the subject.

2. The method of claim 1, wherein the nausea and/or vomiting is caused by the effects of a medication.

3. The method of claim 2, wherein the medication is a chemotherapeutic medicine.

4. The method of claim 1, wherein the THCV is present in an effective human daily dose to reduce or relieve nausea and/or vomiting.

5. The method of claim 4, wherein the effective human daily dose of THCV is between 1 mg and 2000 mg.

6. The method of claim 5, wherein the effective human daily dose of THCV is between 10 mg and 1000 mg.

7. The method of claim 1, wherein the THCV is packaged for use for an extended treatment period.

8. The method of claim 7, wherein the extended treatment period is at least 7 days.

9. The method of claim 1 further comprising administering the THCV in combination with one or more other medicinal substances.

10. The method of claim 1, wherein the THCV is in an isolated or substantially pure form.

11. The method of claim 1, wherein the THCV is in the form of a botanical drug substance.

12. The method of claim 11, wherein all or a substantial proportion of tetrahydrocannabinol (THC) has been removed.

* * * * *